(12) United States Patent
Sparks

(10) Patent No.: US 6,933,126 B2
(45) Date of Patent: Aug. 23, 2005

(54) MEMBRANE TRANSPORTABLE FLUORESCENT SUBSTRATES

(75) Inventor: Alison L. Sparks, North Andover, MA (US)

(73) Assignee: Applera Corporation, Bedford, MA (US)

( * ) Notice: Subject to any disclaimer, the term of this patent is extended or adjusted under 35 U.S.C. 154(b) by 136 days.

(21) Appl. No.: 10/246,678

(22) Filed: Sep. 19, 2002

(65) Prior Publication Data

US 2003/0103902 A1 Jun. 5, 2003

Related U.S. Application Data

(60) Provisional application No. 60/323,077, filed on Sep. 19, 2001.

(51) Int. Cl.[7] ............................. C12Q 1/54; C12N 9/38; A61K 31/785; C12P 21/06
(52) U.S. Cl. ........................ 435/14; 435/207; 435/69.1; 424/486; 424/78.08
(58) Field of Search ................... 435/14, 207; 424/486, 424/78.08

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 5,338,532 A | 8/1994 | Tomalia et al. |
| 5,527,524 A | 6/1996 | Tomalia et al. |
| 5,714,166 A * | 2/1998 | Tomalia et al. ............. 424/486 |

FOREIGN PATENT DOCUMENTS

WO    WO 84/02705    7/1984

OTHER PUBLICATIONS

Nolan et al., "Fluorescence–activated cell analysis and sorting of viable mammalian cells based on beta–D–galactosidase activity after transduction of *E. coli* lacZ," (Proc Natl Acad Sci USA 85:2603–2607, 1988).*

Westmark et al., "Selective monosaccharide transport through lipid bilayers using boronic acid carrieris," J Am Chem Soc 118:11093–11100, 1996.*

(Continued)

*Primary Examiner*—Robert A. Wax
*Assistant Examiner*—Rosanne Kosson
(74) *Attorney, Agent, or Firm*—Steven B. Kelber; Merchant & Gould

(57) ABSTRACT

Intracellular enzyme-activated fluorescent substrates that can be transported into a cell are provided. The membrane transportable fluorescent substrates are complexes (e.g., ionic complexes) formed between an enzyme activated fluorescent substrate and a carrier molecule. The fluorescent substrates can be used in an intracellular assay of enzyme activity and/or expression.

33 Claims, 11 Drawing Sheets

OTHER PUBLICATIONS

Morin et al., "Transport of glycosides through lipid organic membranes mediated by reversible boronate formation is a diffusion–controlled process," J Am Chem Soc116:8895–8901, 1994.*

Stephens, et al., "The Many Ways to Cross the Plasma Membrane", Proc. Nat. Acad. Sci., 98, 8, 4295–4298 (2001).

Haensler, et al., "Polyamidoamine Cascade Polymers Mediate Efficient Transfection Cells in Culture", Bioconjugate Chem., 4, 372–379 (1993).

Boussif, et al., "A Versatile Vector for Gene and Oligonucleotide Transfer Into Cells in Culture and in vivo: Polyethylenimine", Proc. Nat. Acad. Sci. USA, 92, 7297–7301 (1995).

Kabanov, et al., "DNA Complexes with Polycations for the Delivery of Genetic Material Into Cells", Bioconjugate Chem., 6, 7–20 (1995).

Tang, et al., "In Vitro Gene Delivery by Degraded Polyamidoamine Dendrimers", Bioconjugate Chem., 7, 703–714 (1996).

Kukowska–Latallo, et al., "Efficient Transfer of Genetic Material Into Mammalian Cells Using Starburst Polyamidoamine Dendrimers", Proc. Natl. Acad. Sci. USA, 93, 4897–4902 (1996).

Ozaki, et al., "Intracellular Delivery of Phosphoinositides and Inositol Phosphates Using Polyamine Carrires", Proc. Nat. Acad. Sci., 97, 11286–11291 (2000).

Boon, et al., "Facilitated Phosphatidylcholine Flip–Flop Across Erthrocyte Membranes Using Low Molecular Weight Synthetic Translocases", J. AM. Chem. Soc., 123, 6221–6226 (2001).

Wang, et al., "A Novel Biodegradable Gene Carrier Based on Polyphosphoester", J. Am. Chem. Soc., 123, 9480–9481 (2001).

Morin, et al., "Transport of Glycosides Through Liquid Organic Membranes Mediated by Reversible Boronate Formation is a Diffusion–Controlled Process", J. Am. Chem. Soc., 116, 8895–8901 (1994).

Westmark, et al., "Selective Monosaccharide Transport Through Lipid Bilayers Using Boronic Acid Carriers", J. Am. Chem. Soc., 118, 11093–11100 (1996).

* cited by examiner

MEMBRANE TRANSPORTABLE FLUORESCENT SUBSTRATES

CROSS-REFERENCE TO RELATED APPLICATIONS

This application claims priority from U.S. Provisional Application Ser. No. 60/323,077 filed Sep. 19, 2001. The entirety of that provisional application is incorporated herein by reference.

BACKGROUND OF THE INVENTION

1. Field of the Invention

The invention generally relates to the transport of low molecular weight enzyme substrates across lipid membranes of cells and, in particular, to the intracellular transport of fluorescent enzyme substrates.

2. Background of the Technology

It is a general goal of the industry to perform intracellular assays that measure enzyme activity such as enzyme expression and/or enzyme regulation. The enzyme activity can be a direct component of cellular pathways (e.g., hyperexpression of the enzyme due to a specific pathology), or a reporter of cellular function (e.g., reporter gene expression of the enzyme to measure a linked cellular event). In order to perform intracellular assays, improved enzyme-activated, noncytotoxic substrates that efficiently cross the cell membrane are desired. It is also desirable that the assay method enables greater detection sensitivity, a wide dynamic range of detection sensitivity, and ease of cell loading in a non-degradative method for adaptation to high throughput screening applications, as well as other biological and diagnostic assay formats. In view of the foregoing, there is a need for methods and compositions for facilitating the delivery of fluorescent enzyme substrates by complexing with a transporter to detect a variety of enzymes, such as β-glycosidases, esterases, proteases, phosphatases, and oxidases, into cells.

Many techniques have been developed to deliver small and macro molecules into living cells for monitoring or modifying intracellular processes. Most of these methods fall into one of three categories: direct transfer methods, carrier-mediated transfer, and transient cell membrane permeabilization transfer. See, for example, Stephens et al., "The Many Ways to Cross the Plasma Membrane", Proc. Nat. Acad. Sci. USA, 98:8, 4295–4298 (2001). Each of these methods has advantages and disadvantages. The most widely used direct transfer method is glass capillary microinjection where glass micropipettes with a small tip (0.5 mm) are used to inject substances into adherent cells. Microinjection can give transfer efficiencies and cell survival rates up to 100%. Microinjection, however, is technically demanding and has low throughput (e.g., 100–200 cells per experiment) and is limited to adherent cell types. A second transfer method involves permeabilization of the cell membrane using detergents, toxins, UV laser light, or electrical pulses to punch holes in the cell membrane. Once the cell membrane has been permeabilized, substances can move across the cell membrane through the artificial pores by passive diffusion. This approach does not rely on highly skilled manual technique and is amenable to high throughput assays. The drawbacks to this permeabilization method, however, include <50% cell viability, irreversible permeabilization, and disrupted cellular functions of interest. For example, electroporation of cells requires cell suspension which disrupts cell cycle progression, cell adherence, and signal transduction processes.

A third type of transfer utilizes a cell-permeable molecule as a carrier to introduce substances (designated as the "cargo") into cells. The carrier can be covalently coupled or fused to the cargo, or can complex with the cargo to carry the substance into the cell in a piggyback mode. Examples of attached or fused carriers include penetratin, VP22 protein (herpes simplex virus 1), and the TAT protein (HIV-1). A more general approach introduces large molecules (e.g., DNA, RNA or proteins) using cationic lipids such as DOTMA, DOTAP, and DOSPA. As with cell permeabilization methods, carrier-mediated transport is readily adaptable to high throughput assays with minimal technical skill requirements. However, transfer efficiencies often fall below 30% and can vary with cell type. In addition, liposomal delivery can significantly disrupt cellular functions such as lipid metabolism. None of the existing methods provides a complement of desirable transfer characteristics: simplicity, high transfer efficiency, high cell viability, general utility across cell types, and easy automation.

One of the most utilized carrier-mediated transfer methods is DNA transfection of cells using polycationic macromolecules. A variety of natural and synthetic polymers demonstrate an ability to complex with the polyanionic phosphate backbone of DNA to facilitate transport of the charge neutralized complex across the lipid bilayer. Examples of polycationic carrier molecules include spermadine, polylysine, polyethylenimine, "Starburst" PAMAM dendrimers, and polyvinylpyridinium salts such as PVPE and PVPEC. These carrier molecules have varying levels of cytotoxicity and transfection efficiencies. The dendrimers, in particular, exhibit lower cytotoxic effects with higher transfer efficiencies, and thus have been developed into commercially available DNA transfection agents (e.g., "SUPERFECT" and "POLYFECT" activated polyamine dendrimers, which are trademarks of Qiagen N.V.). These materials can serve as alternatives to liposomal carrier formulations. See, for example, Haensler et al., "Polyamidoamine Cascade Polymers Mediate Efficient Transfection of Cells in Culture" Bioconjugate Chem., 4, 372–379 (1993); Boussif et al., "A Versatile Vector for Gene and Oligonucleotide Transfer into Cells in Culture and in Vivo: Polyethyleneimine", Proc. Natl. Acad. Sci. USA, 92, 7297–7301 (1995); Kabanov et al., "DNA Complexes with Polycations for the Delivery of Genetic Material into Cells" Bioconjugate Chem., 6, 7–20 (1995); Tang et al., "In Vitro Gene Delivery by Degraded Polyamidoamine Dendrimers", Bioconjugate Chem., 7, 703–714 (1996); Kukowska-Latallo et al., "Efficient Transfer of Genetic Material into Mammalian Cells Using Starburst Polyamidoamine Dendrimers", Proc. Natl. Acad. Sci. USA, 93:4897–4902 (1996).

Polycationic transport macromolecules have been used to transfer macromolecular substances, such as DNA plasmids, into cells. Several examples of transporting small molecular weight molecules having one to several anionic groups have appeared in the literature. Prestwich et al., for example, describe transporting membrane impermeable phosphatidylinositol polyphosphates and inositol polyphosphates into mammalian, plant, yeast, bacterial, and protozoal cells, using a polyamino dendrimer and type III-S histone as carriers. See Prestwich et al., "Intracellular Delivery of Phosphoinositides and Inositol Phosphates Using Polyamine Carriers", Proc. Nat. Acad. Sci. USA, 97:11286–11291 (2000). The anionic lipids were fluorescently tagged for visualization by fluorescence microscopy. A similar approach has been described using amide and sulfonamide derivatives of the low molecular weight tris(aminoethyl) amine to carry anionic phospholipids as a complex into erythrocytes. Boon et al., "Facilitated Phosphatidylcholine Flip-Flop Across Erythrocyte Membranes Using Low Molecular Weight Synthetic Translocases", J. Am. Chem. Soc., 123, 6221–6226 (2001). The transport decreases headgroup polarity of the phospholipids through complexation to promote diffusion of the phospholipids across the cell membrane. Tris(amidoethyl)amine- and tris(sulfonamidoethyl) amine-mediated transport of dilauroylphosphatidylcholine (DLPC) out of the cell reverts the echinocyte morphology (induced by cellular DLPC uptake) to the initial discocyte shape. The synthetic transporters also carried a fluorescent phosphatidylcholine probe (PC-NBD) into the cell.

U.S. Pat. Nos. 5,338,532; 5,527,524; and 5,714,166 disclose dendrimers (e.g., dense star polymers or starburst polymers) associated with a variety of materials. These materials include drugs, toxins, metal ions, radionuclides, signal generators, signal reflectors, chelated metal, signal absorbers, antibodies, hormones, biological response modifiers, diagnostic opacifiers, fluorescent moieties and scavenging agents. Processes for preparing the conjugates, compositions containing the conjugates and methods of using the conjugates are also disclosed in the aforementioned references.

Although various physical and biological methods have been used to introduce membrane-impermeable exogenous molecules into cells, none of the above-described methods disclose the transport of enzyme active fluorescent substrate complexes across a cell membrane. Moreover, none of the above-described methods disclose delivering a fluorescent substrate complex into a fixed cell for subsequent analysis of one or more fixed cellular components.

In view of the foregoing, there is a need for methods and compositions for facilitating the delivery of fluorescent substrates across the lipid membranes of cells.

SUMMARY OF THE INVENTION

According to a first aspect of the invention, a fluorescent substrate delivery system comprising a complex of an enzyme active fluorescent substrate and a carrier molecule is provided. The fluorescent substrate delivery system can be a polylysine, histone, spermidine, polyamidoamine dendrimers, polyethylenimine, polyethylenimine dendrimers, polyvinylpyridinium salts and polyguanidine peptoids.

According to a second aspect of the invention, a method for detecting the presence of an enzyme in a cell is provided. The method according to this aspect of the invention comprises: contacting a sample comprising the cell with a composition comprising a complex of a carrier molecule and an enzyme active fluorescent substrate comprising a group cleavable by the enzyme; and detecting fluorescence from the sample. The presence of fluorescence indicates the presence of the enzyme in the cell and the intensity of fluorescence indicates the activity or expression of the enzyme in the cell.

According to a third aspect of the invention, a fluorescent substrate comprising at least one ionic group available for complexation through ionic charge interactions with oppositely charged ionic groups on a carrier molecule is provided. The fluorescent substrate can be a fluorescein di-β-D-galactopyranoside (FDG) having ionic substituents, a 4-methylumbelliferyl β-D-galactopyranoside (MUG) having ionic substituents, a resorufin β-D-galactopyranoside having ionic substituents or a 9H-(1,3-dichloro-9,9-dimethylacridin-2-one-7-yl) β-D-galactopyranoside (DDAO galactoside) having ionic substituents. The fluorescent substrate can have a structure as represented by general formula I or general formula II:

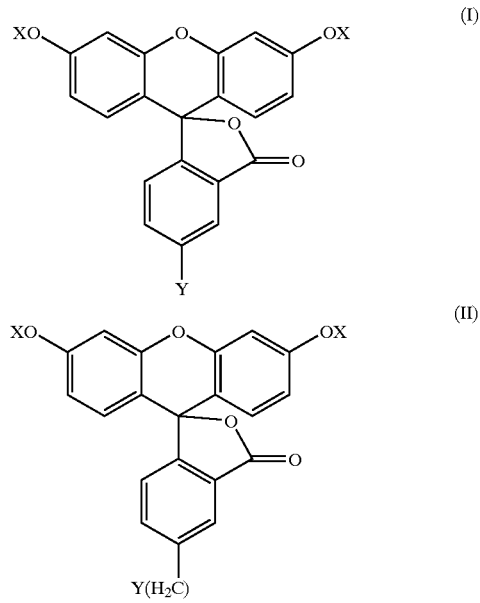

wherein Y represents an anionic or polyanionic group and X represents an enzyme cleavable group.

BRIEF DESCRIPTION OF THE FIGURES

The present invention may be better understood with reference to the accompanying drawings in which.

DETAILED DESCRIPTION OF THE INVENTION

Figure 1A:
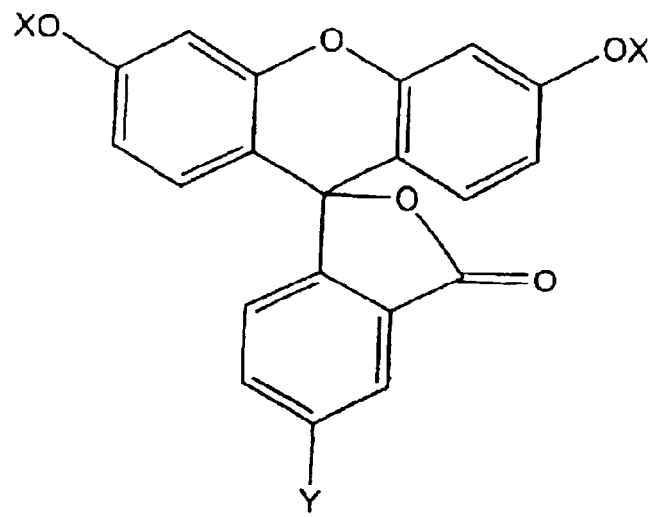
FIG. 1A shows the general formula for a fluorescein substrate having anionic substituents according to a first embodiment of the invention.

It is an object of the invention to provide enzyme-activated fluorescent substrates that can be transported into a cell. The membrane transportable fluorescent substrates according to the invention are ionic complexes formed between an enzyme activatable fluorescent substrate and a transporter molecule. The fluorescent substrates according to the invention can be used in an intracellular assay of enzyme activity and/or expression.

The present invention relates to the transport of low molecular weight enzyme substrates across lipid membranes of cells. The enzyme substrates according to the invention are nonfluorescent substrates which become increasingly fluorescent upon enzyme activation. Cellular uptake of the substrate enables intracellular detection of up- or down-regulation of the target enzyme or detection of expressed enzyme activity in a reporter gene format. In particular, once inside the cell, enzyme cleavage by intracellular hydrolases of the enzyme-labile group, or enzyme oxidation by intracellular oxidases of the enzyme-labile group of the nascent fluorescent substrate yields an increase in fluorescence.

The enzyme-activated fluorescent substrates according to the invention are capable of being transported across the cell membrane without degrading the cell and are therefore useful in detecting the presence or determining the activity of chemical or biological substances in intracellular assays and high throughput intracellular screening formats.

As set forth above, the fluorescent enzyme substrates according to the invention comprise a fluorescent reporter molecule or core having from one to many ionic sites. The ionic sites on the fluorescent core allow the core to be complexed with corresponding ionic sites on a transporter or carrier molecule. The resulting complex can be transported across the cell membrane.

In a preferred embodiment of the invention, the carrier molecule is a polycationic carrier (i.e., a carrier having a plurality of cationic sites). In a further preferred embodiment of the invention, the carrier is a polyamino dendrimer having a plurality of amino functional groups wherein one or more of the amino groups have been protonated to render them cationic.

The fluorescent core of the enzyme substrates according to the invention can be any fluorescent moiety known in the art. For example, the fluorescent core can be fluorescein, rhodamine, 4-methylumbelliferyl, 9H-(1,3-dichloro-9,9-dimethylacridin-2-one-7-yl) (DDAO) or resorufin. The above list is not meant to be limiting, however, and other fluorescent cores can also be used.

The fluorescent enzyme substrates according to the invention have anionic or cationic substituents for complexing to an oppositely charged transporter molecule. For example, fluorescein di-β-D-galactopyranoside (FDG) has two cleavable monosaccharide groups. As the substrate passively diffuses into the cell in low concentrations, cleavage of one saccharide group opens the lactone to a carboxylic acid to form the weakly fluorescing fluorescein mono-β-D-galactopyranoside (FMG). The carboxylic acid forms a carboxylate anion which complexes more efficiently with a polycationic carrier for transport across the cell membrane (both out of and into the cell). As the polycationic carrier loads the FMG into the cell, the intracellular β-galactosidase cleaves the second galactoside to release the strongly fluorescent fluorescein anion.

Alternatively, fluorescent reporter molecules which do not have substituents for complexing to a transporter molecule can be modified to provide the substrate with anionic or cationic substituents. Suitable fluorescent substrates that can be modified according to the invention include, but are not limited to, di-β-D-galactopyranoside (FDG), 4-methylumbelliferyl β-D-galactopyranoside (MUG), resorufin β-D-galactopyranoside and 9H-(1,3-dichloro-9,9-dimethylacridin-2-one-7-yl) β-D-galactopyranoside (DDAO galactoside). The aforementioned fluorescent substrates can become fluorescent upon enzyme activation, for example, when an enzyme such as β-galactosidase cleaves galactose off of the substrate.

Another mode of enzyme-activated fluorescence is a dual enzyme activation where the first enzyme (e.g., intracellular esterase) cleaves an ester to release an intermediate non-fluorescent compound labile to intracellular oxidases. The intracellular oxidases can subsequently oxidize the leuko fluorophore to a fluorescent substrate. Examples of dual enzyme activated substrates that can be modified according to the invention include dihydrofluorescein esters and dihydrorhodamine esters where esterase cleaves the ester groups to release the reduced nonfluorescent substrate for intracellular oxidation by oxidases.

The invention also provides methods of preparing membrane transportable fluorescent substrates. For example, a process for preparing a complex of a membrane transporting substance and a fluorescent substrate comprises contacting the membrane transporting substance with a suitably charged fluorescent substrate to effect a multimolecular moiety bound together by intermolecular ionic charge associations.

The transporter molecule can have a plurality of cationic or anionic sites for complexing the fluorescent substrate. Various substances are known to transport molecules intracellularly and can be used as carrier molecules according to the invention. Examples of such materials include polylysine, polyamidoamine dendrimers (e.g., PAMAM or starburst dendrimers), polyethylenimine, polyethylenimine dendrimers (also known as DAB-Am dendrimers), polyvinylpyridinium salts (e.g., PVPE and PVPEC), polyguanidine peptoids, tris(aminoethyl)amides, tris(aminoethyl) sulfonamides, spermadine, histones, amidinium salts, poly (2-aminoethylpropylene phosphate) and boronic acids. Further, activated dendrimers having charged (e.g., protonated) amino groups such as "SUPERFECT" and "POLYFECT", which are registered trademarks of Qiagen N.V., can also be used as transporter molecules according to the invention. Generally, according to the invention, any amino-terminated dendrimer can be used as a carrier molecule.

In a preferred embodiment of the invention, the carrier molecule is a dendrimer polycation. Dendrimer polycations are three dimensional, highly ordered oligomeric and/or polymeric compounds formed on a core molecule or on a designated initiator. These dendrimers can be synthesized by reiterative reaction sequences adding oligomers and/or polymers. According to a preferred embodiment of the invention, the outer surface of the dendrimer is positively charged to provide sites for complexing with anionic sites on the fluorescent substrate.

In another preferred embodiment, the carrier molecule is a biodegradable polyamine. An example of such a carrier is poly(2-aminoethylpropylene phosphate) (Wang et al., "A Novel Biodegradable Gene Carrier Based on Polyphosphoester" J. Am. Chem. Soc. ASAP publication, September 2001). The advantage of a biodegradable carrier that degrades to noncytotoxic small molecular units further lowers any cytotoxicity.

Polycationic dendrimers can be prepared by known methods. Various methods are disclosed, for example, in PCT/US83/02052 and U.S. Pat. Nos. 4,507,466, 4,558,120, 4,568,737, 4,587,329, 4,631,337, 4,694,064, 4,713,975, 4,737,550, 4,871,779, and 4,857,599.

In general, the terminal groups on the dendrimers used as transporter molecules according to the invention should be capable of acquiring a positive charge. Examples of such groups are azoles, primary, secondary, tertiary and quaternary aliphatic and aromatic amines, pyridines, pyrimidines, pyrazines, guanidines, and combinations thereof. Further, the terminal cationic groups on the dendrimers are preferably covalently attached to the dendrimers. Preferred terminal cationic groups are amine groups and guanidinium groups. However, others may also be utilized. The dendrimer polycations according to the invention can be non-covalently (e.g., ionically) associated with anionic fluorescent substrates. This facilitates disassociation of the complex once it is delivered into the cell.

It is a further object of the invention to synthesize fluorescent substrates which can form ionic complexes with charged membrane transportable substances such as histones, polylysines, and polyamino dendrimers. The enzyme-activated fluorescent substrates according to the invention can have various charged groups available for complexation to multicharged membrane transportable substances. For example, the fluorescent substrate can have one or more anionic charge groups. These anionic groups can include, for example, phosphates, phosphonates, carboxylates, sulfates, sulfonates, phenolates, boronates, and carbonates. These anionic charge groups can complex through ionic charge interactions with cationic charge groups (e.g., protonated polyamino groups) on histones, spermidine, polylysines, polyamidoamine (PAMAM) dendrimers, polyethyleneimine (PEI) dendrimers, guanidinium peptoids, amidinium salts, poly(2-aminoethylpropylene phosphate, tris(aminoethyl)amides, tris(aminoethyl)sulfonamides and boronic acids.

Examples of enzyme-activated fluorescent substrates having anionic groups available for complexation to multicharged (e.g., polycationic) membrane transportable substances according to the invention are shown in the attached figures.

Figure 1B:
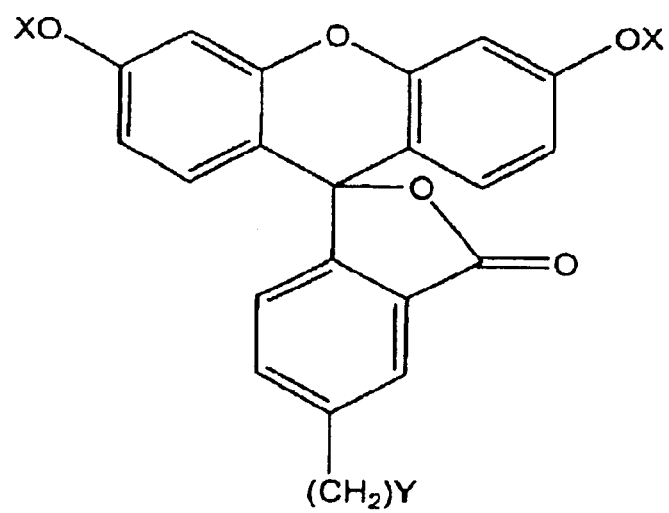
FIG. 1B shows the general formula for a fluorescein substrate having anionic substituents according to a second embodiment of the invention.

FIGS. 1A and 1B show the general formulae for two fluorescein substrates having anionic groups according to the invention. The substituent Y in FIGS. 1A and 1B represents an anionic or polyanionic group. Specific examples of suitable anionic groups include COOH, COO$^-$, SO$_3^-$, OSO$_3^-$, PO$_3^{2-}$, OPO$_3^{2-}$, CONHOH, CONHO$^-$, and poly(maleic acid). The substituent X in FIGS. 1A and 1B represents an enzyme cleavable group such as β-galactoside, β-glucoside, an ester or a phosphate group. The enzyme cleavable group X may also function as an anionic complexing group Y, e.g., where X is phosphate or glucuronide having negative charges.

Figure 2:
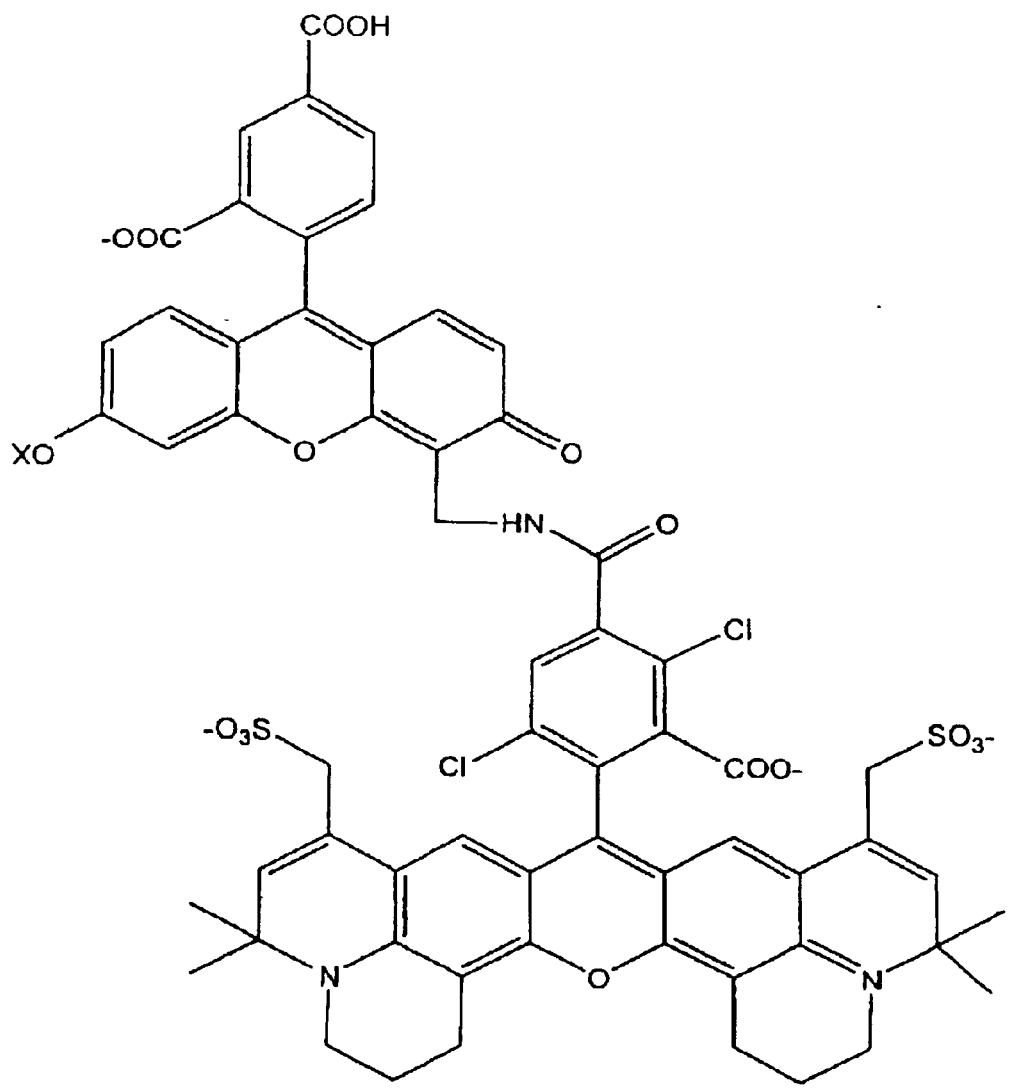
FIG. 2 shows the general formula for a FAM-β-D-galactoside-bis-sulfo-dRAZ substrate having anionic substituents according to the invention.

FIG. 2 shows the general formula for a FAM-β-D-galactoside-bis-sulfo-dRAZ substrate having anionic groups according to the invention. As can be seen from FIG. 2, this fluorescent substrate has four anionic groups—two SO$_3^-$ groups and two COO$^-$ groups. There is also a COOH group which can form a carboxylate anion under appropriate conditions.

Figure 3:
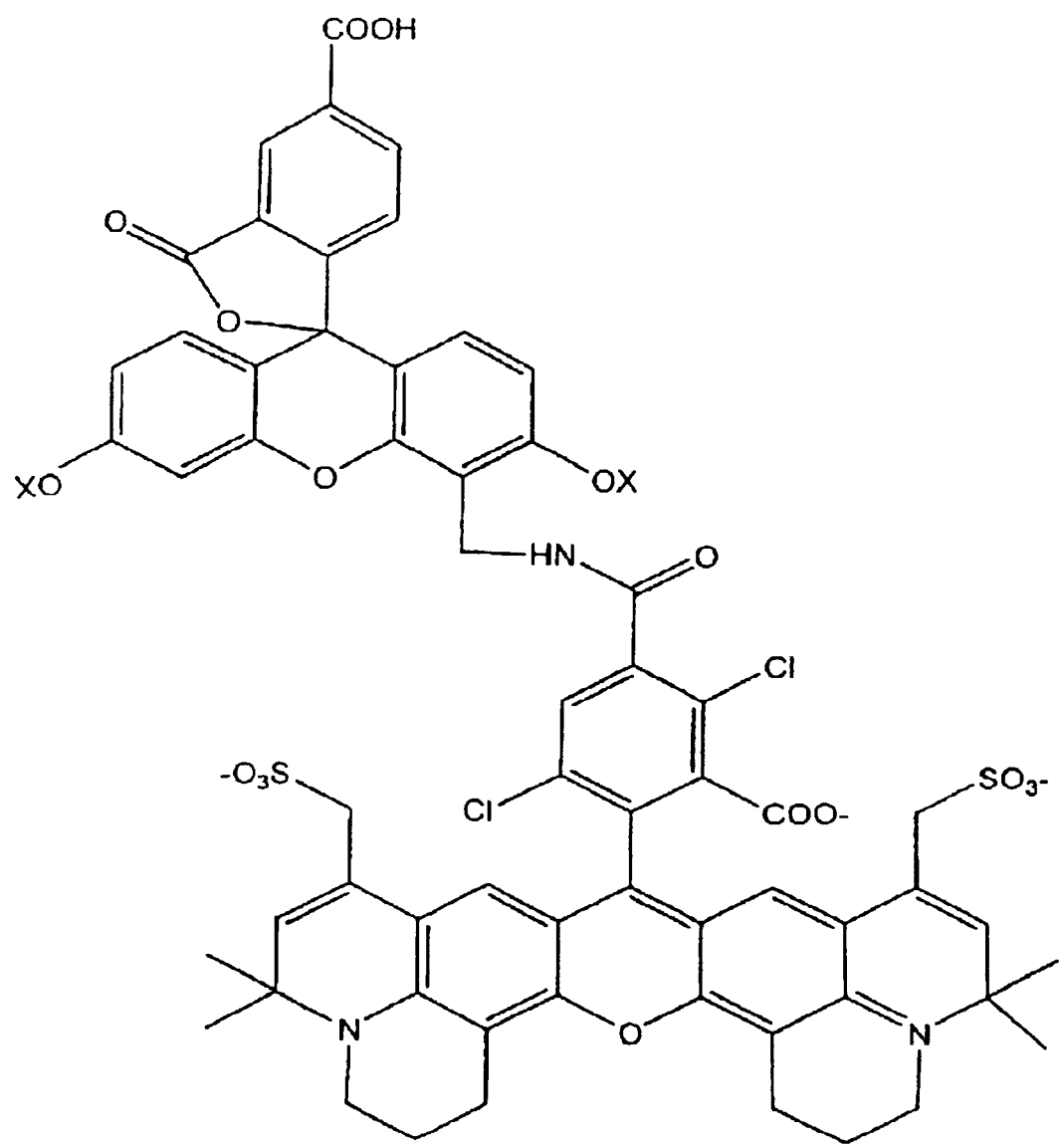
FIG. 3 shows the general formula for a FAM-di-β-D-galactoside-bis-sulfo-dRAZ substrate having anionic substituents according to the invention.

FIG. 3 shows the general formula for a FAM-di-β-D-galactoside-bis-sulfo-dRAZ substrate having anionic groups according to the invention. As can be seen from FIG. 3, this fluorescent substrate has three anionic groups—two SO$_3^-$ charge groups and one COO$^-$ groups. The fluorescent substrate of FIG. 3 also has a COOH group which can form a carboxylate anion under the appropriate conditions.

Figure 4:
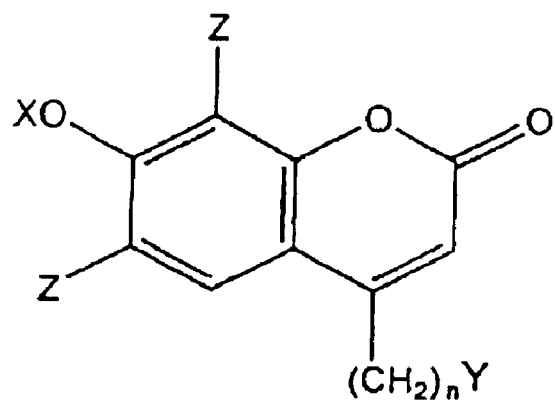
FIG. 4 shows a 4-methylumbelliferyl β-D-galactopyranoside (MUG) substrate having anionic substituents according to the invention.

FIG. 4 shows the general formula for a 4-methylumbelliferyl β-D-galactopyranoside (MUG) substrate having anionic groups according to the invention. The substituent Y in FIG. 4 represents an anionic or polyanionic group which can include COOH, COO$^-$, SO$_3^-$, OSO$_3^-$, PO$_3^{2-}$, OPO$_3^{2-}$, CONHOH, CONHO$^-$ and poly(maleic acid). Z in FIG. 4 represents Cl, F, H or SO$_3^-$ and n is an integer from 0 to 10.

Figure 5:
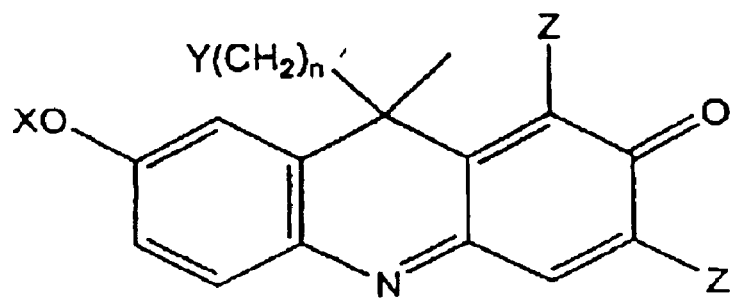
FIG. 5 shows a 9H-(1,3-dichloro-9,9-dimethylacridin-2-one-7-yl) β-D-galactopyranoside (DDAO) substrate having anionic substituents according to the invention.

FIG. 5 shows the general formula for a 9H-(1,3-dichloro-9,9-dimethylacridin-2-one-7-yl) β-D-galactopyranoside (DDAO) substrate having anionic groups according to the invention. The substituent Y in FIG. 5 represents an anionic or polyanionic group which can include COOH, COO$^-$, SO$_3^-$, OSO$_3^-$, PO$_3^{2-}$, OPO$_3^{2-}$, CONHOH, CONHO$^-$ and poly(maleic acid). The substituent Z in FIG. 5 represents Cl, F, H or SO$_3^-$ and n is an integer from 0 to 10.

Figure 6:
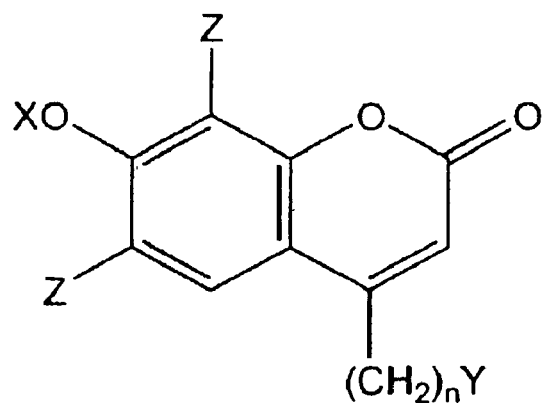
FIG. 6 shows a first embodiment of an anionic fluorescent enzyme substrate based on umbelliferone according to the invention.

FIG. 6 shows a first embodiment of an anionic fluorescent enzyme substrate based on umbelliferone according to the invention.

Figure 7:
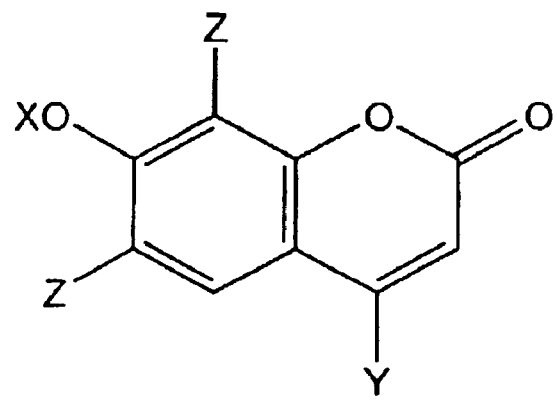
FIG. 7 shows a second embodiment of an anionic fluorescent enzyme substrate based on umbelliferone according to the invention.

FIG. 7 shows a second embodiment of an anionic fluorescent enzyme substrate based on umbelliferone according to the invention. The substituent Z in FIGS. 6 and 7 can be Cl, F, H, or SO$_{3-}$ and n can be an integer from 0 to 10.

The substituent X in FIGS. 2–7 represents an enzyme cleavable group such as β-galactoside, β-glucoside, an ester or a phosphate group. The substituent Y in FIGS. 4, 5, 6 and 7 represents an anionic or polyanionic group which can include COOH, COO$^-$, SO$_3^-$, OSO$_3^-$, PO$_3^{2-}$, OPO$_3^{2-}$, CONHOH, CONHO$^-$, and poly(maleic acid).

Figure 8:
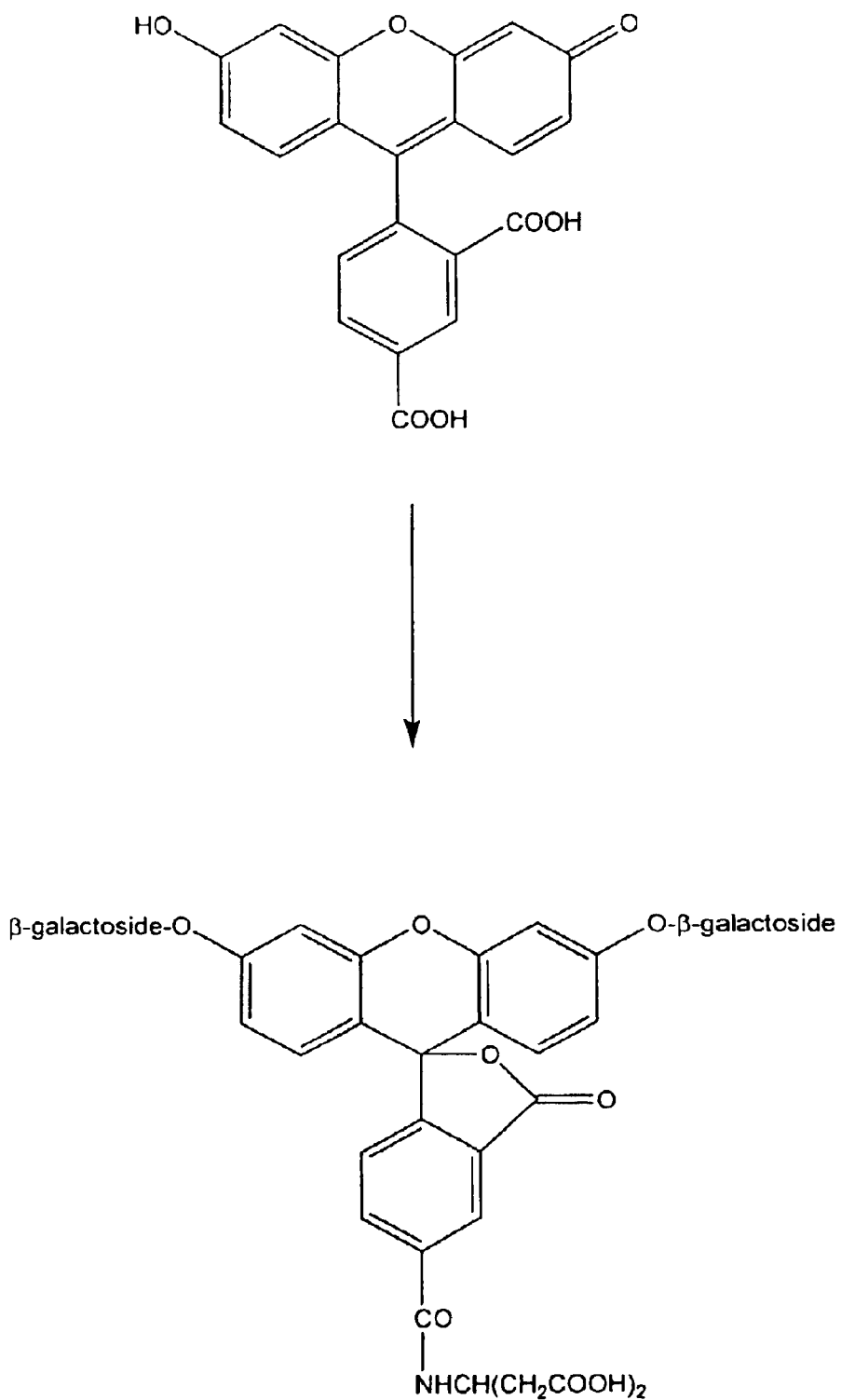
FIG. 8 shows the synthesis of intracellular anionic FDG from 5-carboxyfluorescein.

FIG. 8 shows the synthesis of intracellular anionic FDG from 5-carboxyfluorescein. In a first step of the synthesis, a masked anionic group is coupled to the COOH group in the 5 position of the 5-carboxyfluorescein. Coupling can be carried out, for example, by reacting the 5-carboxyfluorescein with 1 eq. (EtO$_2$C)CH$_2$CH(NH)CH$_2$(CO$_2$Et) and 1.3 eq of a coupling agent (e.g., EDC or DCC) in DMF at room temperature. Alternatively, the 5-N-hydroxysuccinimide ester derived from 5-carboxyfluorescein can be coupled with 1 eq. (EtO$_2$C)CH$_2$CH(NH)CH$_2$(CO$_2$Et), triethylamine, in DMF at room temperature. In a second step of the synthesis, a sugar can be coupled to the product of the first step of the synthesis. Coupling can be carried out, for example, by reaction with 2.5 eq. Ag$_2$CO$_3$, 2.5 eq. sym-collidine and 2.5 eq 2,3,4,6-tetra-O-acetyl-α-D-galactosyl bromide in anhydrous benzene at room temperature. In a third step of the synthesis, the sugar acetates and ethyl esters can be saponified, for example, with NaOMe/MeOH in an anhydrous solvent at room temperature followed by acidic neutralization.

Figure 9:
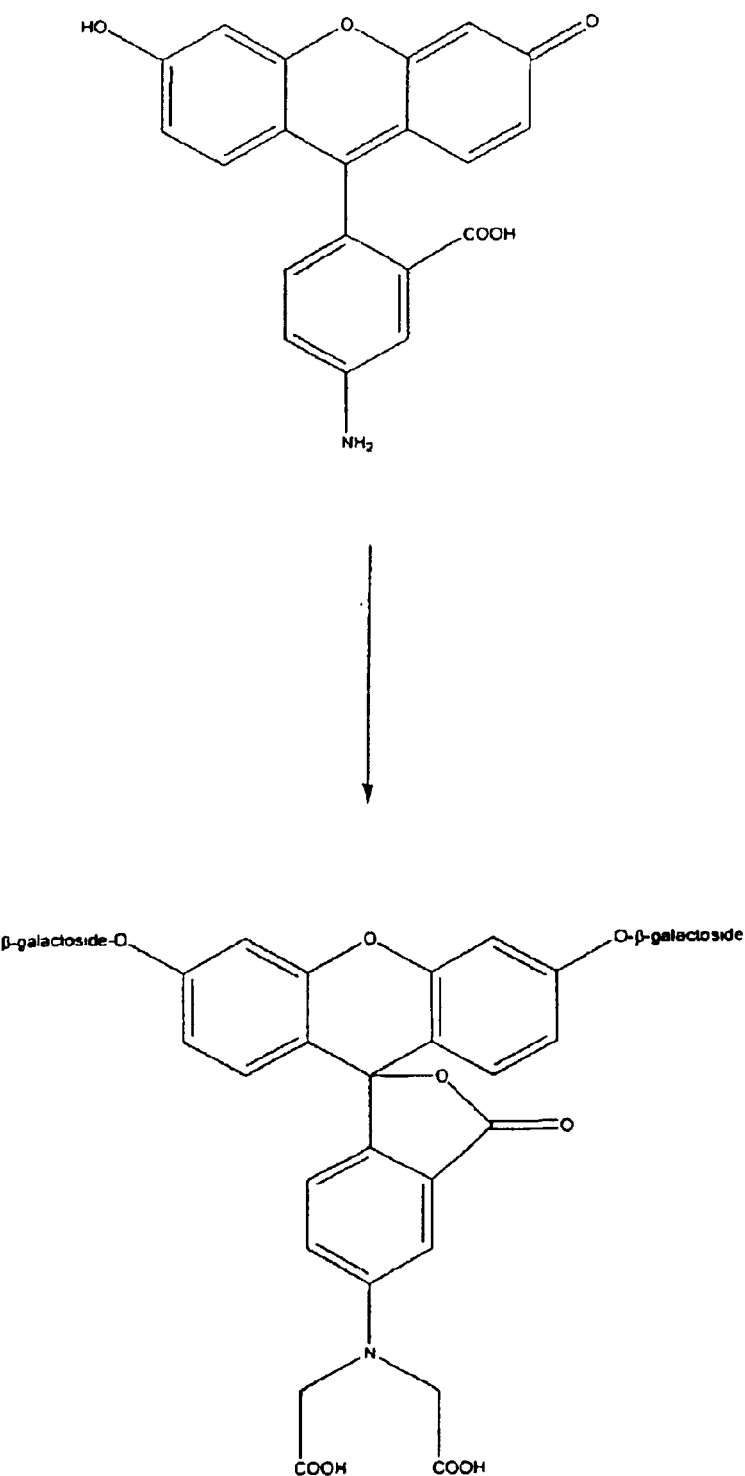
FIG. 9 shows the synthesis of intracellular anionic FDG from 5-aminofluorescein.

FIG. 9 shows the synthesis of intracellular anionic FDG from fluoresceinamine. In a first step of the synthesis, the fluoresceinamine can be dialkylated with a masked anionic group (e.g., using 2.2 eq. BrCH$_2$CO$_2$Et and heat). In a second step of the synthesis, a sugar can be coupled to the product of the first synthesis step by, for example, reaction with 2.5 eq. Ag$_2$CO$_3$, 2.5 eq. sym-collidine, 2.5 eq. 2,3,4,6-tetra-O-acetyl-α-D-galactosyl bromide in anhydrous benzene at room temperature. In a third step of the synthesis, the sugar acetates and ethyl esters can be saponified (e.g., with NaOMe/MeOH in an anhydrous solvent at room temperature) followed by acidic neutralization.

Figure 10:
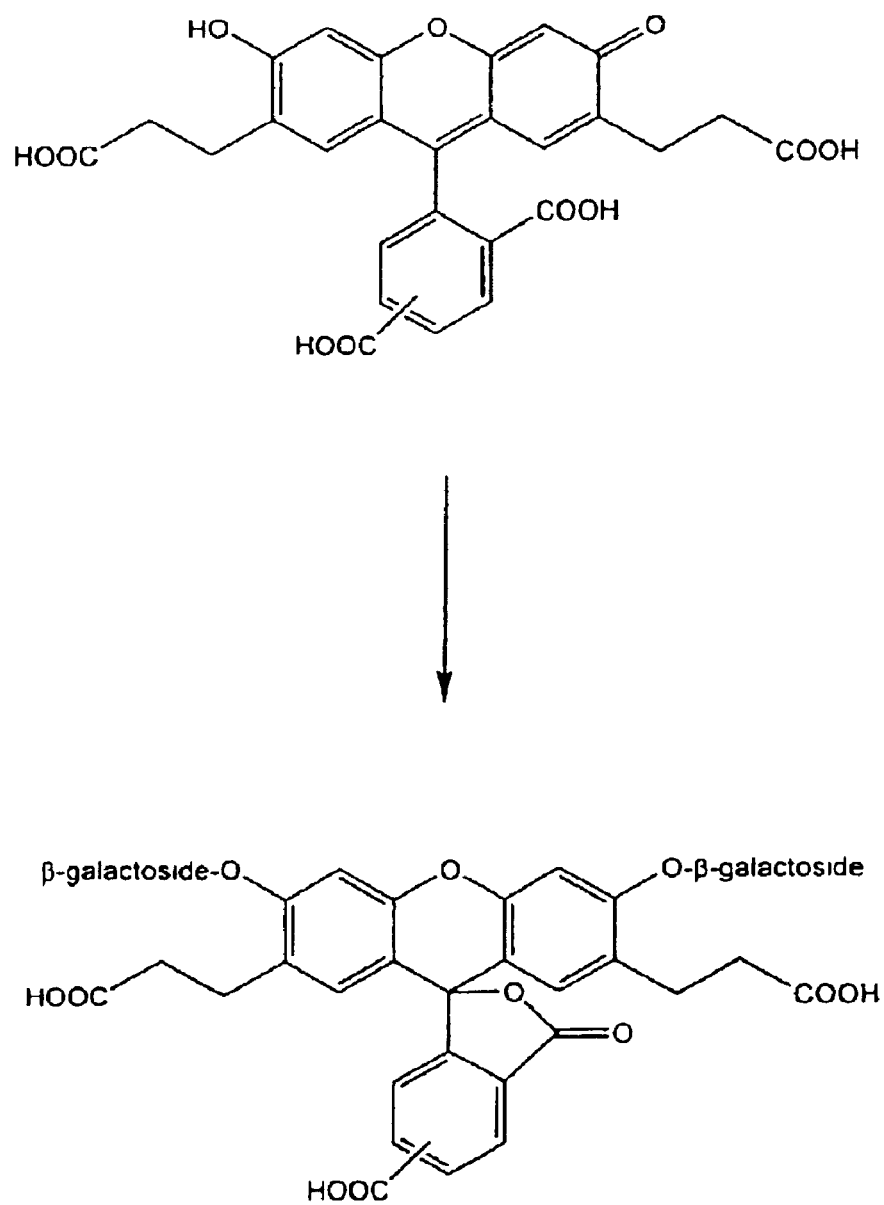
FIG. 10 shows the synthesis of intracellular anionic FDG from 2',7'-bis(2-carboxyethyl)-5-(and-6)-carboxyfluorescein.

FIG. 10 shows the synthesis of intracellular anionic FDG from 2',7'-bis(2-carboxyethyl)-5-(and-6)-carboxyfluorescein. In a first step of the synthesis, the COOH groups can be esterified (e.g., with HCl/MeOH under reflux). In a second step of the synthesis, the sugar can be saponified by, for example, reaction with 2.5 eq. $Ag_2CO_3$, 2.5 eq. sym-collidine, 2.5 eq. 2,3,4,6-tetra-O-acetyl-α-D-galactosyl bromide, in anhydrous benzene at room temperature. In a third step of the synthesis, the sugar acetates and methyl esters can be saponified, for example, with NaOMe/MeOH, in an anhydrous solvent at room temperature followed by acidic neutralization.

Figure 11:
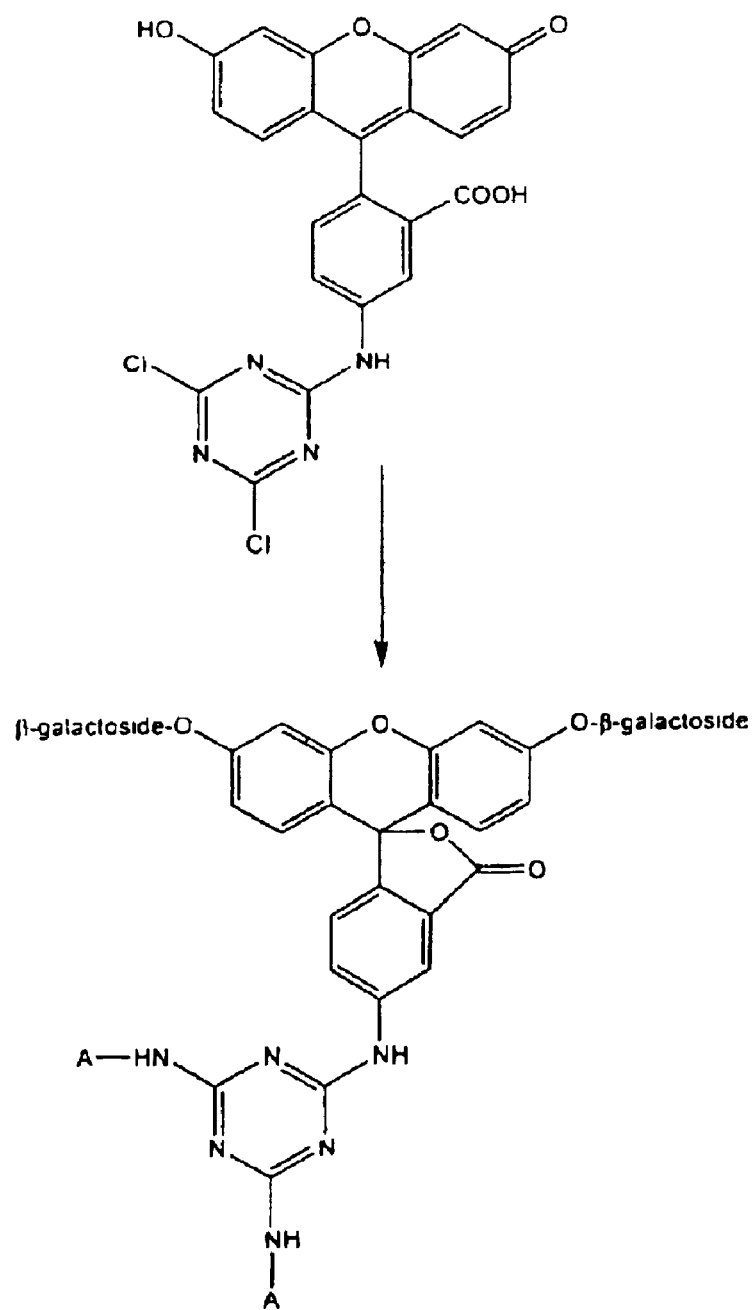
FIG. 11 shows the synthesis of intracellular anionic FDG from 5-(4,6-dichlorotriazinyl)aminofluorescein.
Figure 12:
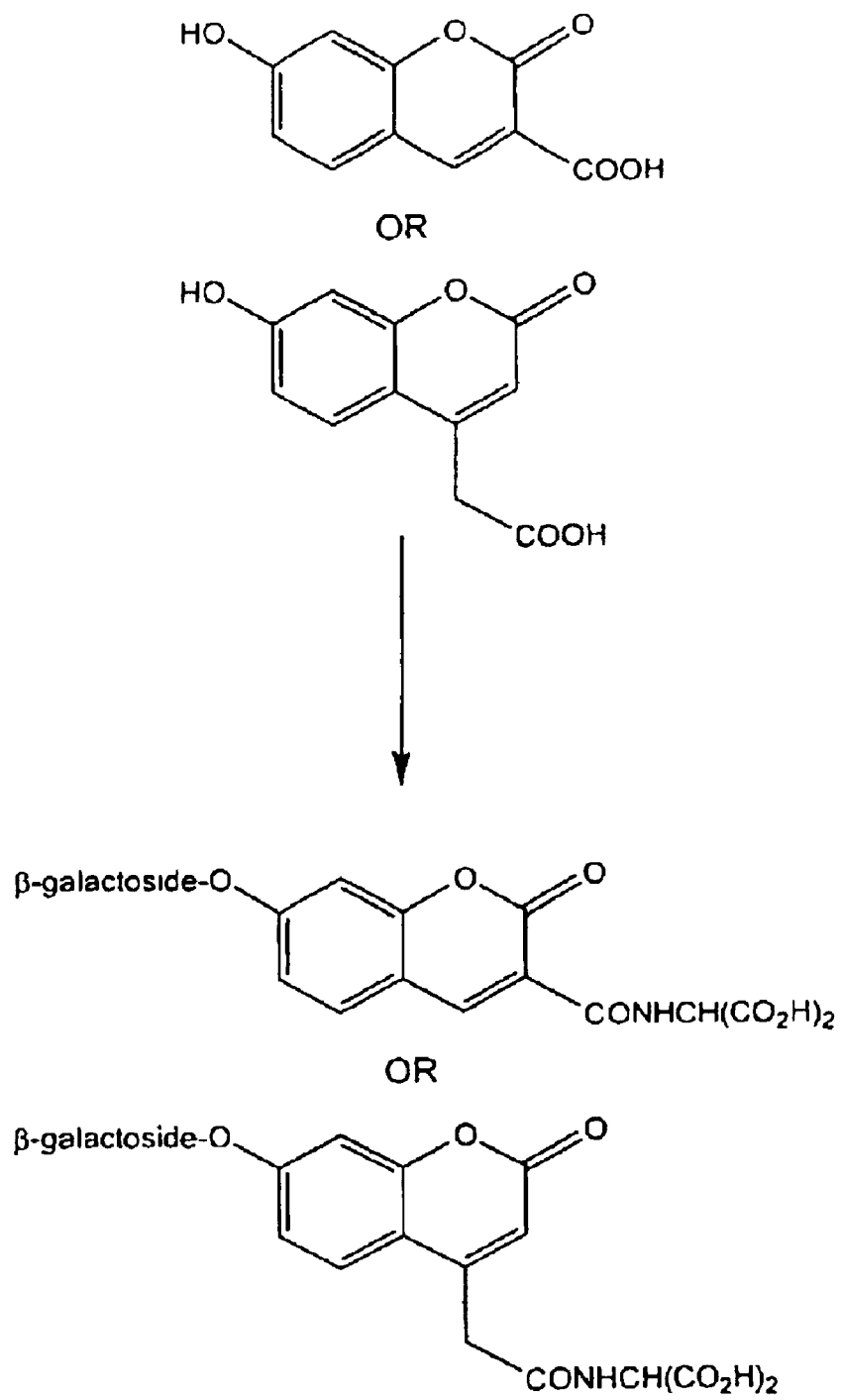
FIG. 12 shows the synthesis of intracellular anionic umbelliferone-galactoside from umbelliferone-3-carboxylic acid or umbelliferone-4-acetic acid.

FIG. 11 shows the synthesis of intracellular anionic FDG from 5-(4,6-dichlorotriazinyl)aminofluorescein. In a first step of the synthesis, the dichlorotriazine is bis-aminated by reaction with a masked anionic group [e.g., using 2.2 eq $NH_2CH_2CO_2Et$ or $NH_2CH(CH_2CO_2Et)_2$] using a hindered amine to scavenge the HCl, (e.g., $nPr_3N$, $nBu_3N$, DBU) in toluene. In a second step of the synthesis, a sugar can be coupled to the reaction product above by, for example, using 2.5 eq $Ag_2CO_3$, 2.5 eq sym-collidine, 2.5 eq 2,3,4,6-tetra-O-acetyl-α-D-galactosyl bromide in anhydrous benzene at room temperature. In a third step of the synthesis, the sugar acetates and ethyl esters can be saponified (e.g., using NaOMe/MeOH, in an anhydrous solvent at room temperature) followed by acidic neutralization. In FIG. 11, the substituents A can be —$CH_2CO_2H$ or —$CH(CH_2CO_2H)_2$ FIG. 12 shows the synthesis of an intracellular anionic umbelliferone-galactoside from umbelliferone-3-carboxylic acid or umbelliferone-4-acetic acid. In a first step of the synthesis according to FIG. 12, a masked anionic group can be coupled to the COOH group by reaction, for example, with 1 eq. ($EtO_2C$)$CH_2CH(NH)CH_2(CO_2Et)$, 1.3 eq coupling agent, (e.g., EDC or DCC) in DMF at room temperature. Alternatively, the 5-N-hydroxysuccinimide ester can be synthesized and coupled with, for example, 1 eq. ($EtO_2C$)$CH_2CH(NH)CH_2(CO_2Et)$, triethylamine, in DMF at room temperature. In a second step of the synthesis, a sugar can be coupled to the reaction product above using, for example, 1.2 eq. $Ag_2CO_3$, 1.2 eq. sym-collidine, 1.2 eq. 2,3,4,6-tetra-O-acetyl-α-D-galactosyl bromide, in anhydrous $CH_3CN$ at room temperature. In a third step of the synthesis, sugar acetates and ethyl esters can be saponified (e.g., with NaOMe/MeOH, in an anhydrous solvent at room temperature) followed by acidic neutralization.

Figure 13:
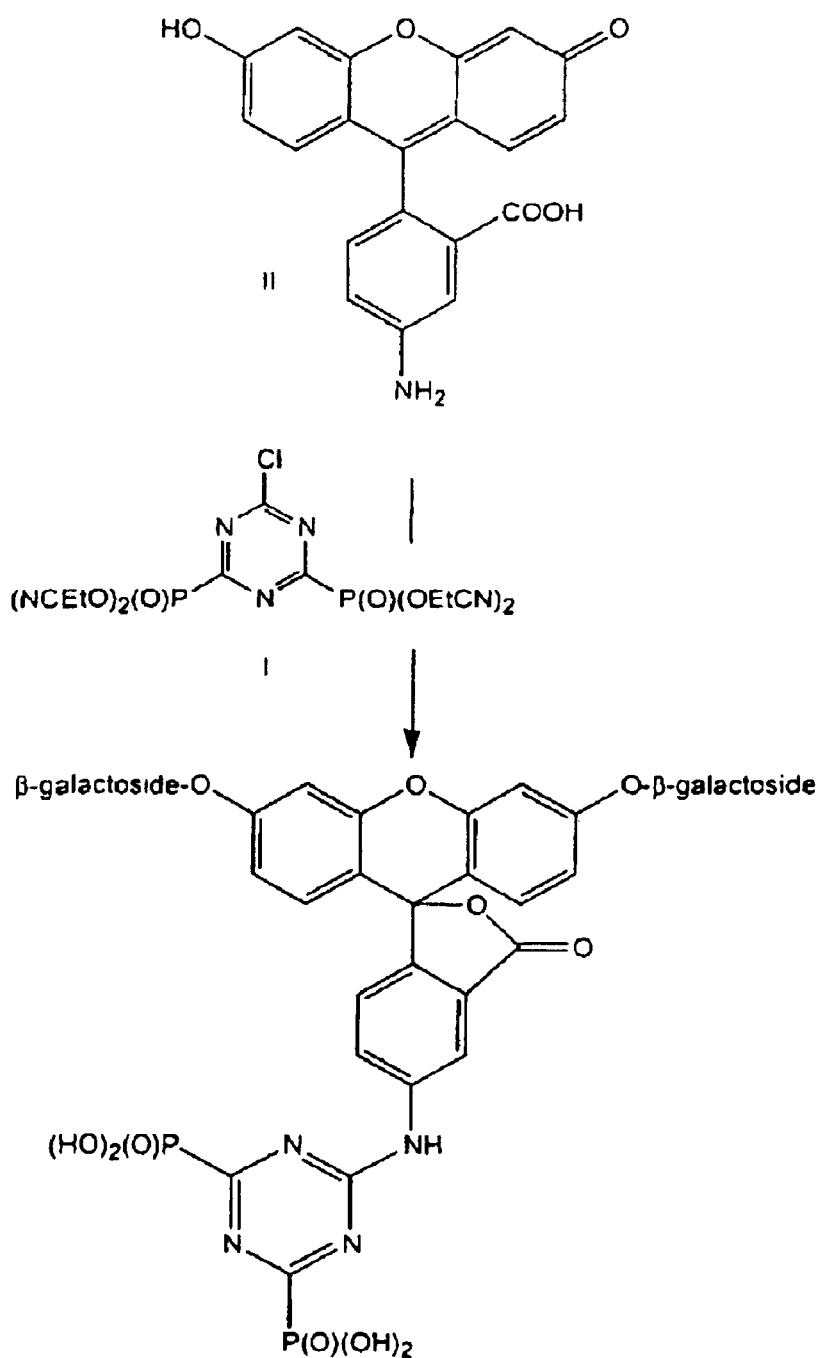
FIG. 13 shows the synthesis of intracellular anionic FDG from phosphonic acid (6-chloro-1,3,5-triazine-2,4-diyl)bis-tetracyanoethyl ester.

FIG. 13 shows the synthesis of intracellular anionic FDG from fluoresceinamine (II). In a first step of the synthesis according to FIG. 13, phosphonic acid (6-chloro-1,3,5-triazine-2,4-diyl)bis-, tetracyanoethyl ester (I) is coupled with fluoresceinamine (II) in MeOH or toluene at room temperature. In a second step of the synthesis, a sugar can be coupled to the reaction product via a Schmidt Imidate procedure (e.g., using $BF_3$—$OEt_2$, 2.2 eq. 2,3,4,6-tetra-O-acetyl-D-galactosyl imidate in $CH_2Cl_2$ at 0° C.). In a third step of the synthesis, the sugar acetates can be saponified and the phosphonates deprotected (e.g., with NaOMe/MeOH in an anhydrous solvent at room temperature) followed by acidic neutralization.

Although anionic charge groups are shown in the figures, the charge groups on the fluorescent substrates can also be cationic having charge groups such as ammonium, phosphonium or sulfonium. For example, one or more cationic charge groups on a fluorescent substrate can complex through ionic charge interactions with anionic charge groups on a membrane transportable substance. A polyanionic carrier would have multiple anionic groups such as $COO^-$, $SO_3^-$, $OSO_3^-$, $PO_3^{2-}$, $OPO_3^{2-}$ and $CONHO^-$. An example of such a membrane-transportable complex would be the association of monomeric, polymeric or dendritic boronic acids with fluorescent substrates, where the fluorescent substrates have at least one monosaccharide substituent (e.g., β-galactoside, β-glucuronoside, or β-mannoside) for complexation to the anionic polymeric boronic acid. Literature examples also report transport of complexes of neutrally charged boronic acids with monosaccharides, although the transport is described as formally occurring through an anionic (boronate) mechanism. See, for example, J. Am. Chem. Soc., 116, 8895–8901 (1994); Chem. Commun., 705–706 (1996); Westmark et al., "Selective Monosaccharide Transport through Lipid Bilayers Using Boronic Acid Carriers", J. Am. Chem. Soc., 118, 11093–11100 (1996). A second example of a boronic acid carrier complex would be the association of a polyboronic acid with fluorescent substrates where Y is a hydroxamic acid group (CONHOH). Since the $pK_a$'s for boronic acids and hydroxamic acids range from 7.5–10.5, a boronic acid/hydroxamic acid complexation system can include either a polyboronic acid carrier (where the cationic substituent Y on the substrate cargo is hydroxamic acid), or a polyhydroxamic acid carrier (where the cationic substituent Y on the substrate cargo is boronic acid).

When the charged fluorescent substrate(s) and the charged membrane transporting substance are mixed, the resulting membrane transportable complex is bound together by ionic charge interactions. As a result, cellular uptake of the overall neutrally charged multimolecular species for subsequent intracellular enzyme assay can be facilitated.

The ability to use the inventive substrates in intracellular assays to detect enzyme activity or expression promises extensive utility as a general tool for biological and diagnostic analyses. For example, bacterial β-galactosidase, encoded by lacZ, and firefly luciferase are widely used reporters for transcriptional activity of eukaryotic promoters in cells. Intracellular detection of β-galactosidase can delineate protein-protein interactions using the β-galactosidase complementation technology disclosed in co-pending application Ser. No. 09/654,499, the entire contents of which are incorporated herein by reference. The fluorescent enzyme substrates would also have utility in cell-based high-throughput screening, e.g., agonist/antagonist ligand binding to cell surface receptors such as GPCRs. Fluctuations in enzyme activity can also identify pathological conditions for diagnostic applications. The inventive membrane transportable fluorescent substrates can be activated by hydrolases such as glycosidases, phosphatases, proteases, sulfatases and esterases.

Prior use of intracellular substrates has been limited by destructive or inefficient cell loading methods, cytotoxic substrates and inadequate detection sensitivities. The present invention solves such deficiencies by providing a) enzyme-activated fluorescent substrates for increased detection sensitivity and increased dynamic detection range; b) membrane transportable substrates for efficient, non-degradative cell-loading.

Many known cell loading methods are destructive to the cell membrane and/or are inefficient, thus rendering them ineffective for in vitro use. Bulk loading procedures include acetoxymethyl ester loading, ATP-induced permeabilization, cationic liposome delivery, electroporation, hypoosmotic shock and scrape loading. Single cell loading procedures such as microinjection and patch pipette perfusion are not compatible with high throughput analyses.

A preferred method of introducing substrates is by transporting the substrate across the cell membrane via a transporter complex into the cell interior and/or into subcellular entities. For example, when using the invention to detect an enzyme in a cell, the cell can be contacted with the fluorescent substrate/transporter complex bearing a group capable of being cleaved by the enzyme being detected. Once the fluorescent substrate complex is transported across the lipid membrane into the cell, the intracellular enzyme cleaves the substrate's enzyme cleavable group to form a fluorescent molecule. It is this increased fluorescence that is detected as an indication of the presence of the enzyme. By measuring the intensity of fluorescence, the expression and/or activity of the enzyme in the cell can be determined.

For example, when using substrates according to the invention to detect an enzyme in a cell, the cell is contacted with the substrate/transporter complex wherein the substrate has a group capable of being cleaved by the enzyme being detected. Once the substrate complex is transported across the lipid membrane into the cell, the intracellular enzyme can cleave the enzyme cleavable group off of the substrate to form a fluorescent molecule. The resulting fluorescence can be detected and is an indication of the presence of the enzyme. By measuring the intensity of fluorescence, the expression and/or activity of the enzyme in the cell can be determined.

The fluorescent substrates according to the invention can have lipophilic substituents that embed the substrate into the cell membrane, thus anchoring the substrate in the cell. The fluorescent substrates according to the invention can also have chloromethyl substituents. These chloromethyl substituents can react with intracellular glutathione to form a tripeptide substrate analogue that tends to remain in the cell. However, the anchored substrates can be more cytotoxic.

A first experiment was conducted to determine the effect of complex formation on FDG detection of β-galactosidase in Psi-2-BAG-α cells. First, FDG detection was measured using FDG without a transporter or carrier complexed thereto (passive load). This measured value was compared to a measurement using a complex of FDG and an activated polyamino dendrimer (e.g., "SUPERFECT", which is a trademark of Qiagen N.V.).

For the passive load test, two vials of cells were prepared. First, two vials each having 330,000 psi-2-BAG-α cells suspended in 250 μl 0.6 mM FDG in Opti-MEM were prepared. A first vial of cells was incubated at 4° C. for 2 hrs and the second vial of cells was incubated at 37° C. for 2 hrs.

For the polyamino dendrimer complex, two vials of cells were prepared in the following manner. First, two vials each having 330,000 psi-2-BAG-α cells suspended in 250 μl 0.6 mM FDG in Opti-MEM containing 25 μl "SUPERFECT" as a polycationic carrier were prepared. The first vial of cells was incubated at 4° C. for 2 hrs and the second vial of cells was incubated at 37° C. for 2 hrs.

Following incubation, 20 μl triplicate samples of the above four cell suspensions (passive/4° C., passive/37° C., "SUPERFECT"/4° C., "SUPERFECT"/37° C.) were added to a 96-well plate.

The 96-well plate was read on a Cytofluor 4000 with excitation filter 485/20 and emission filter 530/25. The data was analyzed as triplicate averages.

| Experiment | Fluorescence (w/o "SUPERFECT") | Fluorescence (w "SUPERFECT") |
| --- | --- | --- |
| Cells + Supernatant, 4° C. | 807 | 8,343 |
| Cells + Supernatant, 37° C. | 2492 | 33,943 |

The above data show that with a Superfect-assisted load of FDG, the fluorescence signal increased 10-fold or more, indicating that a significantly higher amount of the FDG substrate was transported into the cell where β-galactosidase cleavage occurs.

A second experiment was conducted to determine the effect of fluorescent substrate complex formation on FDG detection of rapamycin-induced β-galactosidase complementation in FRAP/FKBPI2 (B14) cells. The cells contain inactive β-galactosidase fragments fused to FRAP and FKBP12 proteins, which upon induction of FRAP and FKBP12 interaction with rapamycin, results in complementation (restoration) of the β-galactosidase activity.

A 96-well plate was plated with FRAP/FKBP12 cells at 10,000 cells per well. Half of the cells were incubated overnight with rapamycin to induce β-galactosidase complementation. The next day, the cells were washed with Opti-MEM. Half of the cells were incubated for 90 min at 37° C. with 254 μl 0.6 mM FDG (fluorescein-di-β-D-galactoside) in Opti-MEM. The remaining cells were incubated 90 min at 37° C. with 0.6 mM FDG, containing "SUPERFECT" as a carrier (14 μl "SUPERFECT" in 240 μl 0.6 mM FDG in Opti-MEM).

The 96-well plate was read on a Cytofluor 4000 with excitation filter 485/20 and emission filter 530/25. The data was analyzed as triplicate averages.

| Experiment | Fluorescence (w/o "SUPERFECT") | Fluorescence (w "SUPERFECT") |
| --- | --- | --- |
| Uninduced Cells | 253 | 338 |
| Induced Cells | 594 | 12,721 |

The above data show that with a "SUPERFECT" assisted load of FDG, the fluorescence signal to noise ratio (S/N) is approximately 37 for the induced cells. This compares to a S/N of about 2 for induced cells detected with an uncomplexed or passive load of FDG (w/o "SUPERFECT"). The above data indicate that a significantly higher amount of the FDG substrate was transported into the cell with "SUPERFECT" for intracellular detection of the rapamycin-induced β-galactosidase expression.

From the foregoing, it will be appreciated that although specific embodiments of the invention have been described herein for purposes of illustration, various modifications may be made without deviating from the spirit and scope of the invention.

What is claimed is:

1. A fluorescent substrate delivery system comprising an ionic complex of an enzyme active fluorescent substrate and a carrier molecule;
   wherein the fluorescent substrate comprises one or more anionic charge groups and the carrier molecule comprises one or more cationic charge groups, and wherein the complex is formed by ionic charge interactions between the one or more anionic charge groups of the fluorescent substrate and the one or more cationic charge groups of the carrier molecule.

2. The fluorescent substrate delivery system of claim 1, wherein the carrier molecule is selected from the group consisting of polylysine, histone, spermidine, polyamidoamine dendrimers, polyethylenimine, polyethylenimine dendrimers, polyvinylpyridinium salts and polyguanidine peptoids.

3. The fluorescent substrate delivery system of claim 1, wherein the one or more anionic charge groups are selected from the group consisting of phosphates, phosphonates, carboxylates, sulfates, sulfonates, phenolates, boronates, and carbonates.

4. The fluorescent substrate delivery system of claim 1, wherein the cationic charge groups comprise protonated polyamino groups.

5. The fluorescent substrate delivery system of claim 1, wherein the fluorescent substrate is selected from the group consisting of a fluorescein di-β-D-galactopyranoside (FDG)

having anionic substituents, a 4-methylumbelliferyl β-D-galactopyranoside (MUG) having anionic substituents, a resorufin β-D-galactopyranoside having ionic substituents and a 9H-(1,3-dichloro-9,9-dimethylacridin-2-one-7-yl) β-D-galactopyranoside substituents.

6. A method for detecting the presence and/or measuring the activity of an enzyme in a cell comprising:

a) contacting a sample comprising the cell with a composition comprising an ionic complex of an enzyme active fluorescent substrate and a carrier molecule, wherein the fluorescent substrate comprises one or more anionic charge groups and the carrier molecule comprises one or more cationic charge groups, and wherein the complex is formed by ionic charge interactions between the one or more anionic charge groups of the fluorescent substrate and the one or more cationic charge groups of the carrier molecule; and b) detecting fluorescence from the sample; wherein the presence of fluorescence indicates the presence of the enzyme in the cell and wherein the intensity of fluorescence indicates the activity or expression of the enzyme in the cell.

7. The method of claim 6, wherein the enzyme cleavable group is cleavable by an enzyme selected from the group consisting of glycosidases, esterases, proteases, oxidases, peptidases and phosphatases.

8. The method of claim 6, wherein the enzyme cleavable group is cleavable by β-galactosidase.

9. The method of claim 6, wherein the fluorescent substrate is selected from the group consisting of a fluorescein di-β-D-galactopyranoside (FDG) having ionic substituents, a 4-methylumbelliferyl β-D-galactopyranoside (MUG) having ionic substituents, a resorufin β-D-galactopyranoside having ionic substituents and a 9H-(1,3-dichloro-9,9-dimethylacridin-2-one-7-yl) β-D-galactopyranoside (DDAO galactoside) having ionic substituents.

10. The fluorescent substrate delivery system of claim 1, wherein the fluorescent substrate further comprises lipophilic substituents capable of anchoring the substrate to a cell membrane.

11. The fluorescent substrate delivery system of claim 1, wherein the fluorescent substrate further comprises chloromethyl substituents.

12. The fluorescent substrate delivery system of claim 1, wherein the fluorescent substrate has a structure as represented by general formula I or general formula II:

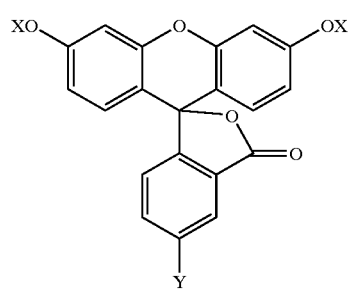

(I)

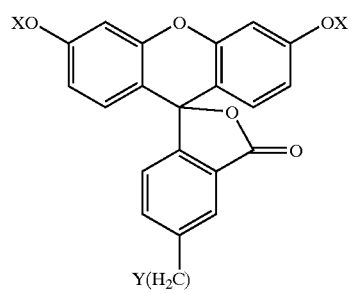

(II)

wherein Y represents an anionic or polyanionic group and X represents an enzyme cleavable group.

13. The fluorescent substrate delivery system of claim 12, wherein Y comprises an anionic group selected from the group consisting of COOH, COO⁻, $SO_3^-$, $OSO_3^-$, $PO_3^{2-}$, $OPO_3^{2-}$, CONHOH, CONHO⁻, and poly(maleic acid).

14. The fluorescent substrate delivery system of claim 12, wherein each X is independently selected from the group consisting of a β-galactoside residue, a β-glucoside residue, an ester and a phosphate group.

15. The fluorescent substrate delivery system of claim 12, wherein each X is independently a phosphate having negative charges or a glucuronide having negative charges.

16. The fluorescent substrate delivery system of claim 1, wherein the fluorescent substrate has a structure as represented by general formula III or the general formula IV:

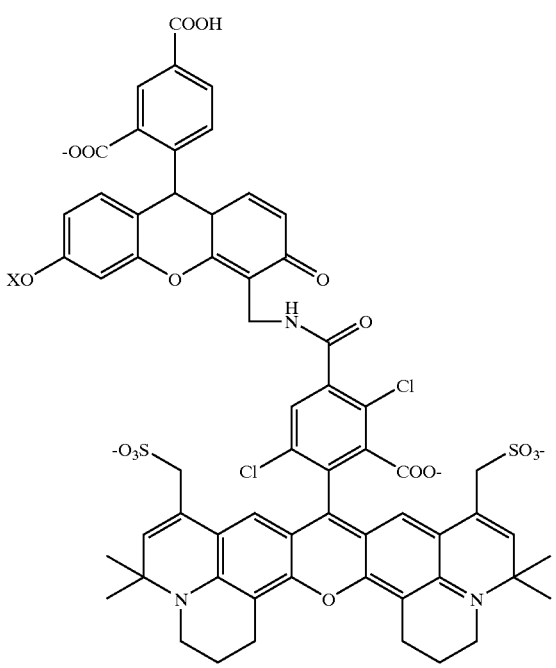

(III)

15

-continued

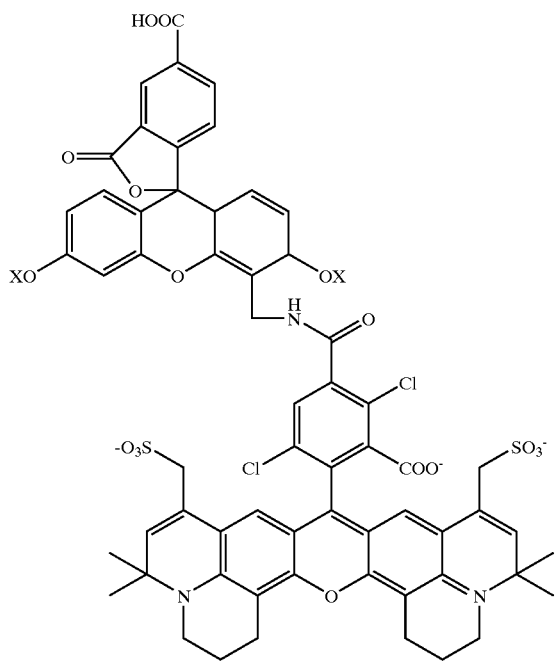

(IV)

wherein X represents an enzyme cleavable group.

17. The fluorescent substrate delivery system of claim 16, wherein each X is independently selected from the group consisting of a β-galactoside residue, a β-glucoside residue, an ester and a phosphate group.

18. The fluorescent substrate delivery system of claim 16, wherein each X is independently a phosphate having negative charges or a glucuronide having negative charges.

19. The fluorescent substrate delivery system of claim 1, wherein the fluorescent substrate has a structure as represented by general formula V or the general formula VI:

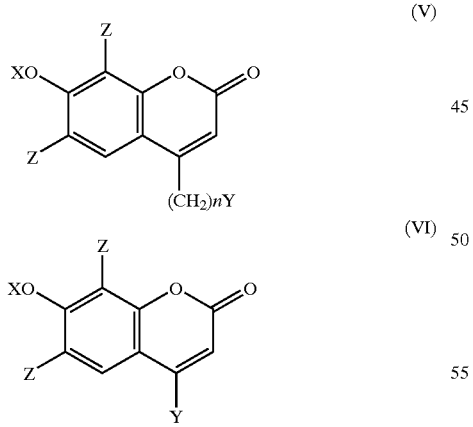

(V)

(VI)

wherein Y represents an anionic or polyanionic group, X represents an enzyme cleavable group, each Z independently represents Cl, F, H or $SO_3^-$, and n is an integer from 0 to 10.

20. The fluorescent substrate delivery system of claim 19, wherein Y comprises an anionic group selected from the group consisting of COOH, $COO^-$, $SO_3^-$, $OSO_3^-$, $PO_3^{2-}$, $OPO_3^{2-}$, CONHOH, $CONHO^-$, and poly(maleic acid).

21. The fluorescent substrate delivery system of claim 19, wherein each X is independently selected from the group

16 consisting of a β-galactoside residue, a β-glucoside residue, an ester and a phosphate group.

22. The fluorescent substrate delivery system of claim 19, wherein each X is independently a phosphate having negative charges or a glucuronide having negative charges.

23. The fluorescent substrate delivery system of claim 1, wherein the fluorescent substrate has a structure as represented by general formula VII:

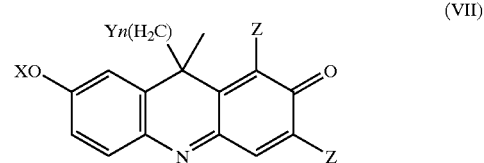

(VII)

wherein Y represents an anionic or polyanionic group, X represents an enzyme cleavable group, each Z independently represents Cl, F, H or $SO_3^-$, and n is an integer from 0 to 10.

24. The fluorescent substrate delivery system of claim 23, wherein Y comprises an anionic group selected from the group consisting of COOH, $COO^-$, $SO_3^-$, $OSO_3^-$, $PO_3^{2-}$, $OPO_3^{2-}$, CONHOH, $CONHO^-$, and poly(maleic acid).

25. The fluorescent substrate delivery system of claim 23, wherein each X is independently selected from the group consisting of a β-galactoside residue, a β-glucoside residue, an ester and a phosphate group.

26. The fluorescent substrate delivery system of claim 23, wherein each X is independently a phosphate having negative charges or a glucuronide having negative charges.

27. The fluorescent substrate delivery system OF claim 1, wherein the fluorescent substrate has a structure as represented by general formula VIII or general formula IX:

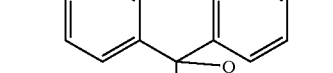

(VIII)

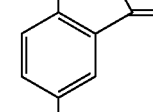

(IX)

wherein X represents an enzyme cleavable group.

28. The fluorescent substrate delivery system of claim 27, wherein the enzyme cleavable group is a β-galactoside residue.

29. The fluorescent substrate delivery system of claim 1, wherein the fluorescent substrate has a structure as represented by general formula X or general formula XI:

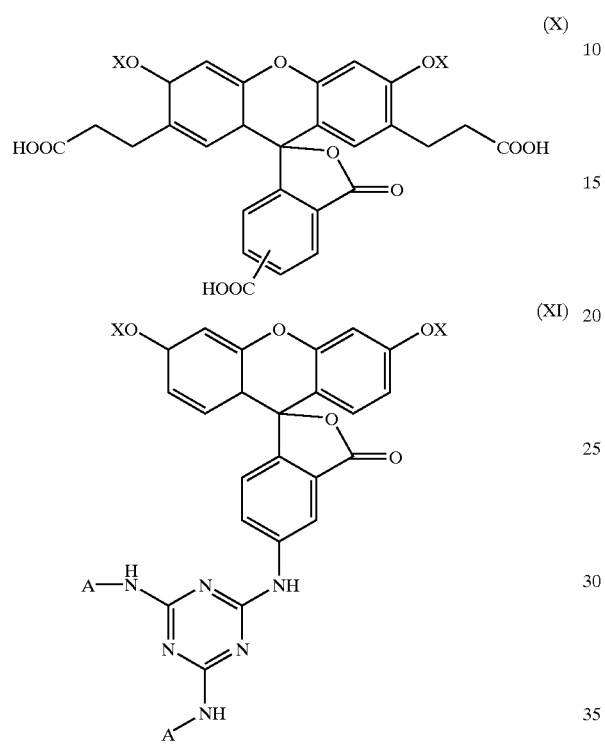

wherein X represents an enzyme cleavable group and each "A" substituent independently represents —CH₂CO₂H or —CH(CH₂CO₂H)₂.

30. The fluorescent substrate delivery system of claim 1, wherein the fluorescent substrate has a structure as represented by general formula XII:

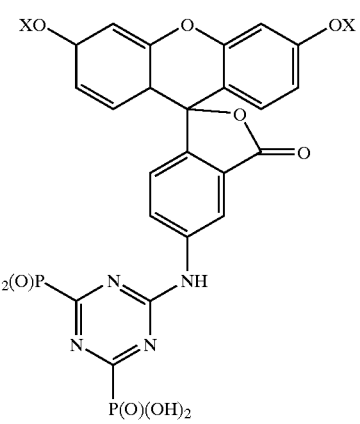

wherein X represents an enzyme cleavable group.

31. The fluorescent substrate delivery system of claim 30, wherein the enzyme cleavable group is a β-galactoside residue.

32. The fluorescent substrate delivery system of claim 1, wherein the fluorescent substrate has a structure as represented by general formula XIII or the general formula XIV:

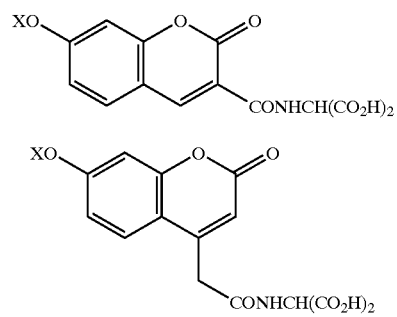

wherein X represents an enzyme cleavable group.

33. The fluorescent substrate delivery system of claim 32, wherein the enzyme cleavable group is a β-galactoside residue.

* * * * *